(12) United States Patent
Shin et al.

(10) Patent No.: US 10,444,246 B2
(45) Date of Patent: Oct. 15, 2019

(54) KIT FOR MEASURING TITER OF A PROTEIN COMPRISING HUMAN FC USING INDIRECT ELISA AND METHOD FOR MEASURING TITER OF A PROTEIN COMPRISING HUMAN FC USING THE SAME

(71) Applicant: GREEN CROSS CORPORATION, Yongin-si, Gyeonggi-do (KR)

(72) Inventors: Yong Won Shin, Yongin-si (KR); Juho Lee, Yongin-si (KR); Jeong-Ae Lim, Yongin-si (KR); Ki Hwan Chang, Yongin-si (KR); Min-Soo Kim, Yongin-si (KR)

(73) Assignee: GREEN CROSS CORPORATION, Yongin-si (KR)

( * ) Notice: Subject to any disclaimer, the term of this patent is extended or adjusted under 35 U.S.C. 154(b) by 170 days.

(21) Appl. No.: 15/515,714

(22) PCT Filed: Sep. 30, 2015

(86) PCT No.: PCT/KR2015/010324
§ 371 (c)(1),
(2) Date: Mar. 30, 2017

(87) PCT Pub. No.: WO2016/053002
PCT Pub. Date: Apr. 7, 2016

(65) Prior Publication Data
US 2017/0307630 A1    Oct. 26, 2017

(30) Foreign Application Priority Data
Sep. 30, 2014   (KR) .......................... 10-2014-0131456

(51) Int. Cl.
*G01N 33/68*   (2006.01)
*G01N 33/543*  (2006.01)

(52) U.S. Cl.
CPC ... *G01N 33/6857* (2013.01); *G01N 33/54393* (2013.01); *G01N 33/6827* (2013.01); *G01N 2333/02* (2013.01)

(58) Field of Classification Search
CPC ........... G01N 33/6857; G01N 33/6827; G01N 33/54393; G01N 2333/02
See application file for complete search history.

(56) References Cited

U.S. PATENT DOCUMENTS

| | | | |
|---|---|---|---|
| 5,599,543 A * | 2/1997 | Hoffman ............... | C07K 5/1008 424/191.1 |
| 5,801,064 A | 9/1998 | Foresman et al. | |
| 6,670,159 B1 | 12/2003 | Savage et al. | |
| 2008/0299045 A1 | 12/2008 | Jeon et al. | |
| 2014/0193432 A1 | 7/2014 | Nakamura et al. | |
| 2014/0341917 A1* | 11/2014 | Nastri ................ | A61K 39/3955 424/139.1 |

FOREIGN PATENT DOCUMENTS

| | | | |
|---|---|---|---|
| CN | 101368973 A | * | 2/2009 |
| EP | 0 806 667 A1 | | 11/1997 |
| JP | 07504492 A | | 5/1995 |
| JP | 08182497 A | | 7/1996 |
| JP | 10502165 A | | 2/1998 |
| JP | 2008527332 A | | 7/2008 |
| KR | 10-2004-0021768 A | | 3/2004 |
| KR | 10-0467706 B1 | | 1/2005 |
| KR | 10-1072895 B1 | | 10/2011 |
| KR | 10-2013-0063229 A | | 6/2013 |
| WO | 00/73347 A1 | | 12/2000 |

OTHER PUBLICATIONS

European Patent Office, Communication dated Feb. 2, 2018, issued in corresponding European Application No. 15845586.5.
State Intellectual Property Office of the P.R.C., Communication dated Apr. 2, 2018, issued in corresponding Chinese Application No. 201580058076.2.
Shin et al., "Human monoclonal antibody against Hepatitis B virus surface antigen (HBsAg)", Antiviral Research 75 (2007), pp. 113-120.
Japan Patent Office, Communication dated May 15, 2018 (draft date of Apr. 26, 2018), issued in corresponding Japanese Application No. 2017-516170.
Abdullah S. El-Madhun et al., "Systemic and local immune responses after parenteral influenza vaccination in juvenile diabetic patients and healthy controls: results from a pilot study", Vaccine, 1998, pp. 156-160, vol. 16, No. 2/3.
Lars R. Haaheim et al., "Antibodies from lymphocytes used as diagnostic markers: a novel approach", International Congress Series, 2001, pp. 283-289, vol. 1219.
Odd Odinsen., "Antibody Detection and Kinetics of Antibody Production during Early Stages of Immunization with Hepatitis B Virus Vaccine", Clin. Vaccine Immunol., Dec. 2007, pp. 1623-1628, No. 14, No. 12.
Peter Kryger et al., "Enzyme-Linked Immunosorbent Assay for Detection of Immunoglobulin M Antibody to Hepatitis B Core Antigen", Journal of Clinical Microbiology, Mar. 1981, pp. 405-409, vol. 13, No. 3.
International Searching Authority, International Search Report for PCT/KR2015/010324, dated Jan. 18, 2016.

* cited by examiner

Primary Examiner — Shafiqul Haq
(74) Attorney, Agent, or Firm — Sughrue Mion, PLLC

(57) ABSTRACT

Provided are a kit for measuring a titer of a human antibody, a humanized antibody, or a human Fc-fusion protein in human plasma or serum, and a method for measuring a titer of a human Fc-containing protein in human plasma or serum using the same, and more specifically, a kit for measuring a titer of human Fc-containing protein in human plasma or serum, the kit including a diluent for sample, a diluent for conjugate, and a cleansing solution and being used in analysis through an indirect enzyme-linked immunosorbent assay (indirect ELISA), and a method for measuring a titer of human Fc-containing protein in human plasma or serum using the same.

20 Claims, 4 Drawing Sheets

KIT FOR MEASURING TITER OF A PROTEIN COMPRISING HUMAN FC USING INDIRECT ELISA AND METHOD FOR MEASURING TITER OF A PROTEIN COMPRISING HUMAN FC USING THE SAME

CROSS REFERENCE TO RELATED APPLICATIONS

This is a National Stage of International Application No. PCT/KR2015/010324 filed Sep. 30, 2015, claiming priority based on Korean Patent Application No. 10-2014-0131456 filed Sep. 30, 2014, the contents of all of which are incorporated herein by reference in their entirety.

TECHNICAL FIELD

The present invention relates to a kit for measuring a titer of a protein comprising human Fc and a method for measuring a titer of a protein comprising human Fc using the same, and more specifically, to a kit for measuring a titer of a protein comprising human Fc in human plasma or serum, the kit including a diluent for sample, a diluent for conjugate, and a cleansing solution and being used in analysis through an indirect enzyme-linked immunosorbent assay (hereinafter, referred to as an indirect ELISA), and a method for measuring a titer of a protein comprising human Fc in human plasma or serum using the same.

BACKGROUND ART

An anti-hepatitis B virus surface antigen antibody (anti-HBsAg antibody) is produced after infection of hepatitis B virus or vaccination of hepatitis B virus vaccine, and used to monitor results of hepatitis B virus vaccine by measuring a concentration of the produced anti-HBs antibody through anti-HBs antibody titer test (anti-HBs concentration of 10 mIU/mL or less is determined as a non-immune anti-HBs concentration). In addition, in a liver transplant having hepatitis B by hepatitis B virus as an underlying disease, the anti-HBsAg antibody is used to monitor a titer of the anti-HBs antibody at the time of administrating hepatitis B immunoglobulin (HBIG) in order to prevent reinfection of the hepatitis B virus.

As a method for analyzing a titer of the anti-HBs antibody, there are an enzyme immunoassay (EIA), chemiluminescent microparticle immunoassay (CMIA), radioimmunoassay (RIA), and the like. (El-Madhun et al., Vaccine, 16:156-160, 1998; L. Haaheim et al., International Congress Series, 1219:283-289, 2001; Odd Odinsen et al., Clin. Vaccine Immunol., 14(10):1623-1628, 2007; P. Kryger et al., J. Clin. Microbiol., 13:405-409, 1981).

The method for analyzing the titer of the anti-HBs antibody is to measure the titer of the antibody by coating a surface antigen (HBsAg) of the hepatitis B virus on a microwell plate or microparticles, reacting the surface antigen with a sample to be measured, and then measuring an amount of color development, luminescence, or isotopes by using the surface antigen (HBsAg) of the hepatitis B virus conjugated with an enzyme or a radioactive isotope.

IgG which is a representative antibody has a Y shape. As illustrated in FIG. 1A, antigen binding sites are present at both ends of the Y shape, such that the antigens are bound to each site. As illustrated FIG. 1A, measuring the titer is normally performed when a surface antigen of the hepatitis B virus coated on the bottom (hereinafter, referred to as a coated HBsAg) is bound to one site of the antigen binding sites of the anti-HBs antibody, and a surface antigen of the hepatitis B virus labeled with an enzyme or a radioactive isotope (hereinafter, referred to as a labeled HBsAg) is bound to the other site, that is, when the surface antigens are bound to each site.

However, when measuring a titer of the anti-HBs monoclonal antibody developed by Green Cross Corp., according to a method illustrated in FIG. 1A without human plasma or serum, the measured titer is about 20 to 100 times lower than that of a method illustrated in FIG. 1D. It is thought that the reason that the anti-HBs titer of the anti-HBs monoclonal antibody measured by the method of FIG. 1A is lower may actually come from an error possibility due to a combination such as FIG. 1B or FIG. 1C. That is, a case in which two binding sites of the antibody to be measured are bound to both of the coated HBsAg or the labeled HBsAg (FIG. 1B), or a case in which one binding site of the antibody is not capable of being bound to one antigen when the other binding site of the antibody is bound to the antigen (FIG. 1C) may occur, and accordingly, an amount of the antibody may not be accurately measured.

In addition, even though the titer is measured by the method illustrated in FIG. 1D to overcome the above-described problems, when a fully human antibody such as the anti-HBs monoclonal antibody developed by Green Cross Corp., is used, non-specific binding of the fully human antibody with other human antibodies originally present in human plasma or serum may occur as illustrated in FIG. 2, and a secondary antibody recognizing a protein comprising human Fc is not capable of differentiating the non-specific binding and a specific binding of the anti-HBs monoclonal antibody, which causes high background noise, and accordingly, it is still difficult to normally measure the titer.

In order to solve the above-described disadvantages, the present inventors found that measurement error may be reduced by accurately measuring only specific reactions such as FIG. 1D through the method for measuring a titer based on indirect ELISA; however, precision in the measurement of the antibody titer among test subjects is still low.

Accordingly, the present inventors made an effort to exclude error possibility of the existing titer measurement and increase precision in the titer measurement of the a protein comprising human Fc in the human plasma or serum, and as a result, found that when a kit for measuring a titer of a protein comprising human Fc including a diluent for sample, a diluent for conjugate, and a cleansing solution each having a specific composition, is used, the error possibility in measuring the titer of the a protein comprising human Fc in the human plasma or serum is remarkably decreased, and the precision in the measurement of the antibody titer among test subjects is increased, and completed the present invention.

DISCLOSURE

Technical Problem

An object of the present invention is to provide a kit for measuring a titer of a protein comprising human Fc capable of increasing precision in measuring a titer of a human antibody, a humanized antibody, or a human Fc-fusion protein in human plasma or serum, and a method for measuring a titer of a protein comprising human Fc, in particular, an antibody, in human plasma or serum using the same.

Technical Solution

In order to achieve the foregoing objects, the present invention provides a kit for measuring a titer of a protein comprising human Fc including:

(a) a diluent for sample including bovine serum, skim milk, and non-ionic surfactant;

(b) a diluent for conjugate including animal-derived serum; and (c) a cleansing solution including sodium acetate, sodium chloride, and non-ionic surfactant.

The present invention also provides a method for measuring a titer of a protein comprising human Fc, the method including:

(a) diluting a sample including a protein comprising human Fc by using a diluent for sample;

(b) adding and reacting standard solutions diluted with various concentrations and the diluent for sample in wells of a plate to which a target antigen is adsorbed;

(c) suctioning contents of each of the wells and washing each of the wells with a cleansing solution;

(d) completely removing the cleansing solution remaining in each of the wells, and adding a diluent for conjugate in each of the wells to be subjected to a reaction;

(e) suctioning contents of each of the wells and washing each of the wells with the cleansing solution;

(f) completely removing the cleansing solution remaining in each of the wells, and adding a substrate solution in each of the wells to be subjected to a reaction;

(g) stopping a reaction by adding a solution for stopping reaction in each of the wells; and (h) measuring absorbance of the standard solutions and the sample.

BEST MODE

As long as it is not defined in other ways, all technical and scientific terms used in the present specification have the same meaning as being generally appreciated by those skilled in the art to which the present invention pertains. In general, the nomenclature used in the present specification is well known in technical fields and generally used.

The present invention provides a novel method for measuring a titer of a protein comprising human Fc, capable of remarkably decreasing errors occurring by non-specific bindings with human antibodies originally present in human plasma or serum and having more accurate values as compared to the existing measurement method on an antibody having high affinity to a specific antigen, and a kit for measuring the titer of the a protein comprising human Fc.

The protein comprising human Fc in the present invention means all proteins including human Fc region.

The a protein comprising human Fc may be at least one selected from the group consisting of a human antibody, a humanized antibody, a chimeric antibody, and a Fc-fusion protein such as etanercept, in which soluble receptor, cytokine, hormone, and the like, are fused with Fc, but is not limited thereto. The human antibody and the humanized antibody are particularly preferred as examples of the protein comprising human Fc.

"Hepabig-Gene ELISA" or "H-E" in the present specification means a kit for measuring a titer of the protein comprising human Fc of the present invention.

In an exemplary embodiment of the present invention, measurement precision and accuracy of the kit for measuring the titer of the a protein comprising human Fc of the present invention were confirmed by comparing analysis results using the kit for measuring the titer of the a protein comprising human Fc and analysis results using the existing anti-HBs antibody titer measurement (hereinafter, RIA (AMC) measurement).

Hereinafter, the kit for measuring the titer of the a protein comprising human Fc and the measuring method according to the present invention are described in detail by explaining a kit for measuring a titer of an anti-HBs antibody as an example.

Figure 1:
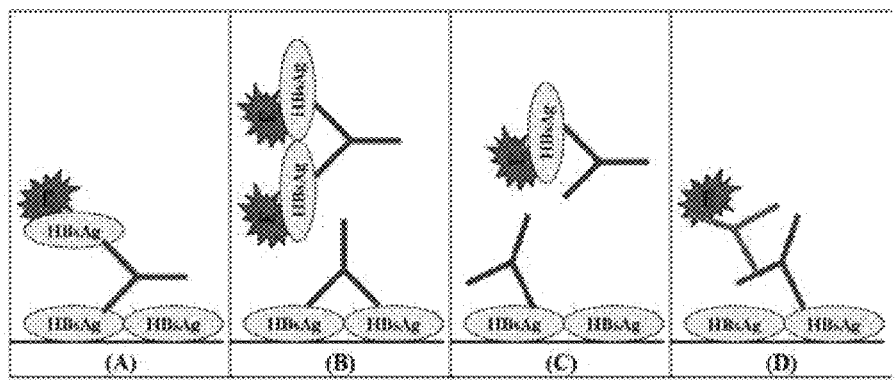
FIG. 1 is a schematic diagram illustrating a process for measuring an antibody titer of a hepatitis B virus surface antibody (anti-HBs).
Figure 2:
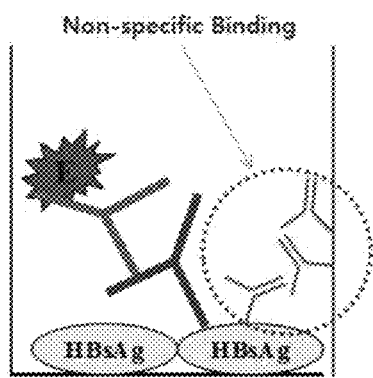
FIG. 2 is a schematic diagram illustrating a problem in human plasma or human serum in the existing method for measuring the titer of the anti-HBs.
Figure 3:
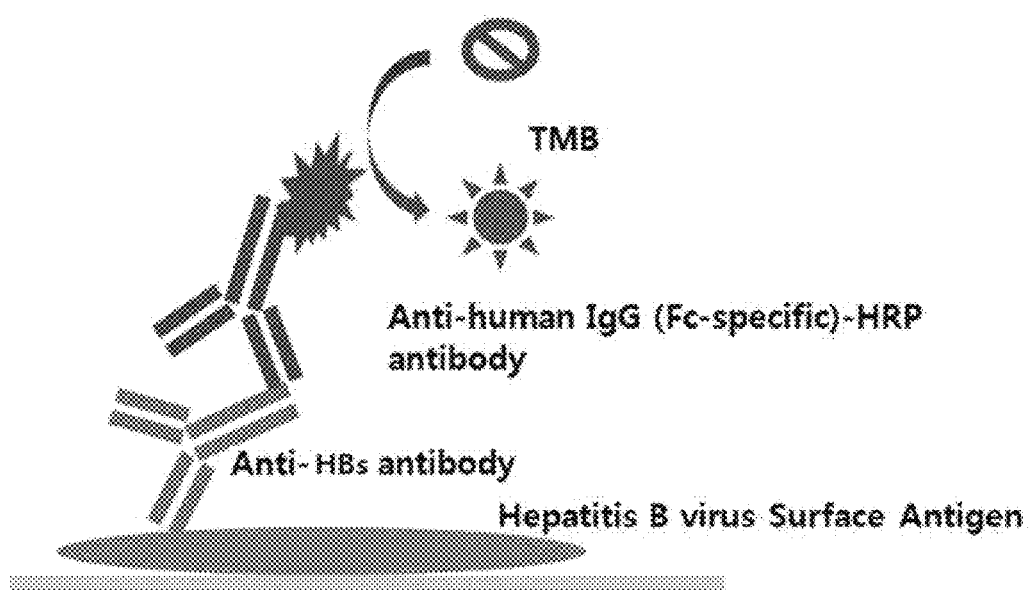
FIG. 3 is a schematic diagram illustrating a process for measuring the titer of the anti-HBs antibody according to the present invention.

In the conventional method for measuring the titer of the anti-HBs antibody, as illustrated in FIG. 1A, the titer could be measured in a proper way when a surface antigen of the hepatitis B virus is bound to one site of the antigen binding sites of the anti-HBs antibody coated on the bottom, and a surface antigen of the hepatitis B virus labeled with an enzyme or a radioactive isotope is bound to the other site of the antigen binding sites, respectively.

However, when measuring a titer of an anti-HBs monoclonal antibody developed by Green Cross Corp., according to a method illustrated in FIG. 1A, the measured titer is about 20 to 100 times lower than that of a method illustrated in FIG. 1D (data not shown). It is thought that the reason that the anti-HBs titer of the anti-HBs monoclonal antibody measured by the method of FIG. 1A is lower may actually come from an error possibility such as FIG. 1B or FIG. 1C. Accordingly, the present inventors practiced a test for measuring an antibody titer using a method illustrated in FIG. 1D in order to exclude error possibilities (FIGS. 1B and 1C) of the existing titer measurement, and found that the antibody titer could be accurately measured in the method illustrated in FIG. 1D as compared to the existing methods.

Recently, patients receiving a liver transplant due to hepatitis B are periodically administered with hepatitis B human immunoglobulin plasma fraction preparations in order to prevent recurrence of Hepatitis B. Time for re-administration is determined through periodic monitoring in serum based on 500 mIU/mL measured by the existing RIA (AMC) measurement. However, since the anti-HBs titer measurement is also the same as the method illustrated in FIG. 1A, it is impossible to measure an accurate titer of GC1102 (see Korean Patent No. 467706) which is a human monoclonal antibody.

In addition, when hepatitis B human immunoglobulin plasma fraction preparations are periodically administered in the patients receiving the liver transplant due to hepatitis B, the titer is increased in the plasma or the serum up to thousands of mIU/mL. The existing conventional anti-HBs titer measurement method has a measurable range from 10 mIU/mL to the maximum of 1,000 mIU/mL, and accordingly, the plasma or the serum needs to be additionally diluted to confirm an accurate titer, and accuracy and precision according to the dilution may be changed depending on diluent for samples, and accordingly, a separate verification for sample dilution is needed.

Therefore, the present invention attempted to find out correlation between analysis results of RIA (AMC) measurement and analysis results of the analysis method, that is, the method for measuring the titer of the antibody, using hepatitis B immune human globulin by national standards, and possibility that 500 mIU/mL of anti-HBs antibody titer in patient serum which is the basis for re-administration of the hepatitis B human immunoglobulin plasma fraction preparations is also equally applicable to Hepabig-Gene ELISA, and the possibility of securing accuracy and precision even at a wide range at the time of applying the diluent for sample according to the present invention.

In an exemplary embodiment of the present invention, when the antibody titer is measured using the national standards through the kit for measuring the antibody titer using indirect ELISA according to the present invention, a recovery rate (%) was about 93.3% as compared to an actual value, and the titer up to 3,500 mIU/mL was capable of being accurately measured. When the antibody titer is measured using the hepatitis B human immunoglobulin national standards through the existing RIA (AMC) measurement, the titer value was 1.4 times higher than the actual value. Accordingly, it was confirmed that the indirect ELISA using the kit for measuring the antibody titer according to the present invention is capable of measuring the titer more accurately at a wider range as compared to the existing RIA (AMC) measurement.

In another exemplary embodiment of the present invention, it may be confirmed that measuring a titer of an anti-HBs antibody in rat serum is possible by using the kit for measuring the titer of Fc-containing protein according to the present invention. It means that the titer is capable of being measured with high precision even in measuring the titer of antibodies or Fc-containing protein derived from specific animal species similar to the present invention, in plasma or serum of the same animal species.

In one general aspect, a kit for measuring a titer of a protein comprising human Fc includes:

(a) a diluent for sample including bovine serum, skim milk, and non-ionic surfactant;

(b) a diluent for conjugate including animal-derived serum; and (c) a cleansing solution including sodium acetate, sodium chloride, and non-ionic surfactant.

In the present invention, the bovine serum of the diluent for sample may have a concentration of 5 to 100% (w/v). In addition, the skim milk of the diluent for sample may have a concentration of 0.05 to 0.2% (w/v). When the concentration of skim milk is higher than the above-described range, primary diluent is excessively sticky, which increases measurement error, and when the concentration of the bovine serum and skim milk is lower than the above-described range, possibility of non-specific binding may be increased, the non-specific binding in which a protein comprising human Fc, an antibody to be detected, is bound to undesirable site of protein, or antigen. Preferably, the concentration of the bovine serum and skim milk may be 10% (w/v) and 0.1% (w/v), respectively.

The non-ionic surfactant of the diluent for sample may be used without limitation as long as it corresponds to objects of the present invention. Preferably, the non-ionic surfactant of the diluent for sample may be at least one selected from the group consisting of Tween 20 (polysorbate 20), Tween 80 (polysorbate 80), Brij 30 (polyoxyethylene(4) lauryl ether), Brij 35 (polyoxyethylene(23)lauryl ether). The most preferably, Tween 20 may be used. The non-ionic surfactant may have a concentration of 0.025 to 0.1% (w/v), preferably, 0.05% (w/v).

The diluent for sample may further include a preservative, preferably, Proclin300, but is not limited thereto. When the preservative is added, the preservative may have a concentration of 0.025 to 0.1% (w/v), preferably, 0.05% (w/v).

In the present invention, the animal-derived serum of the diluent for conjugate is preferably a goat serum, but is not limited thereto. That is, all animal-derived serums may be used as long as it corresponds to objects of the present invention.

The goat serum may include goat anti-human IgG, and the goat anti-human IgG may be specific to Fc, and may be antibody fragments of whole IgG or Fab, or the like. Preferably, the goat anti-human IgG of the diluent for conjugate may be specific to Fc.

The diluent for conjugate may include the animal-derived serum at a concentration of 5 to 20% (w/v).

In the present invention, the sodium acetate of the cleansing solution may have a concentration of 10 to 40 mM, the sodium chloride of the cleansing solution may have a concentration of 75 to 300 mM, the non-ionic surfactant of the cleansing solution may have a concentration of 0.025 to 0.1% (w/v), and a pH of the cleansing solution may be 3 to 5. Preferably, the sodium acetate may have a concentration of 20 mM, the sodium chloride may have a concentration of 150 mM, the non-ionic surfactant may have a concentration of 0.05% (w/v), and pH of the cleansing solution may be 4.

The non-ionic surfactant of the cleansing solution may be used without limitation as long as it corresponds to objects of the present invention. Preferably, the non-ionic surfactant of the cleansing solution may be at least one selected from the group consisting of Tween 20 (polysorbate 20), Tween 80 (polysorbate 80), Brij 30 (polyoxyethylene(4) lauryl ether), Brij 35 (polyoxyethylene(23)lauryl ether), and the like. The most preferably, Tween 20 may be used.

In another general aspect, a method for measuring a titer of a protein comprising human Fc includes:

(a) diluting a sample including a protein comprising human Fc by using a diluent for sample;

(b) reacting standard solutions diluted with various concentrations and the diluent for sample in wells of a plate to which a target antigen is adsorbed;

(c) suctioning contents of each of the wells and washing each of the wells with a cleansing solution;

(d) completely removing the cleansing solution remaining in each of the wells, and adding a diluent for conjugate in each of the wells to be subjected to a reaction;

(e) suctioning contents of each of the wells and washing each of the wells with the cleansing solution;

(f) completely removing the cleansing solution remaining in each of the wells, and adding a substrate solution in each of the wells to be subjected to a reaction;

(g) stopping a reaction by adding a solution for stopping reaction in each of the wells; and (h) measuring absorbance of the standard solutions and the sample.

In the present invention, the diluent for sample includes bovine serum, skim milk, and non-ionic surfactant, wherein the bovine serum of the diluent for sample may have a concentration of 5 to 100% (w/v), the skim milk of the diluent for sample may have a concentration of 0.05 to 0.2% (w/v), and the non-ionic surfactant of the diluent for sample may have a concentration of 0.025 to 0.1% (w/v).

The diluent for sample may further include a preservative, preferably, Proclin300, wherein the preservative may have a concentration of 0.025 to 0.1% (w/v).

The diluting of the sample using the diluent for sample in step (a) may be performed by using the diluent for sample having a volume by about 2 to 20 times, preferably, 5 to 15 times, and the most preferably, 10 times, larger than that of the sample. Further, the sample including the a protein comprising human Fc may be one or more selected from the group consisting of human serum, human plasma and human blood, but is not limited thereto.

In the present invention, the diluent for conjugate includes an animal-derived serum, preferably, a goat serum, but is not limited thereto. That is, all animal-derived serums may be used as long as it corresponds to objects of the present invention.

The goat serum may include goat anti-human IgG, and the goat anti-human IgG may be specific to Fab or Fc. Preferably, the goat anti-human IgG of the diluent for conjugate may be specific to Fc.

Titer values of the standard solution diluted with various concentrations may be 1000, 500, 150, 100, 50, 10, and 0 mIU/ml.

The diluent for conjugate may be a goat serum, and the goat serum may have a concentration of 5 to 20% (w/v).

The cleansing solution may include sodium acetate, sodium chloride, and non-ionic surfactant.

The sodium acetate of the cleansing solution may have a concentration of 10 to 40 mM, the sodium chloride of the cleansing solution may have a concentration of 75 to 300 mM, the non-ionic surfactant of the cleansing solution may have a concentration of 0.025 to 0.1% (w/v), and pH of the cleansing solution may be 4.

Step (b) may be performed at room temperature for 10 to 120 minutes, preferably, 30 to 90 minutes, and the most preferably, 60 minutes. Steps (d) and (f) may be performed at room temperature for 10 to 60 minutes, preferably, 20 to 40 minutes, and the most preferably, 30 minutes.

Absorbance in step (h) is preferably measured at measurement wavelength of 450 nm and reference wavelength of 620 nm within 30 minutes after adding a solution for stopping reaction, but is not limited thereto.

The substrate solution of step (f) is TMB peroxidase substrate, preferably, at least one selected from TMB A and TMB B, and particularly, the most preferably, a mixture of TMB A and TMB B, but is not limited thereto. It is obvious to a person skilled in the art that all of general substrate solutions are usable.

The a solution for stopping reaction of step (g) is usable without limitation as long as it stops color development of the substrate, preferably, sulfuric acid solution, but is not limited thereto.

EXAMPLE

Hereinafter, the present invention will be described in detail with reference to the following Examples. However, the following examples are only for exemplifying the present invention, and it will be obvious to those skilled in the art that the scope of the present invention is not construed to be limited to these examples.

Example 1: Measurement of Titer in Human Serum by Hepabig-Gene ELISA

An object of the present Example is to confirm reduction of background noise and confirm whether it is possible to normally measure a titer of an anti-HBs antibody in human serum by measuring the titer of the anti-HBs antibody in human serum using Hepabig-Gene ELISA and comparing the obtained titer with a titer measured by general ELISA using BSA/PBS.

Reagents used for the present Example are as follows.
(1) Anti-HBs Antibody
GC1102 titer standard (GCC, Lot. N787R8003, 10,500 mIU/mL, Korean Patent No. 467706)
HB48-33 (Korean Patent No. 1072895)
HB48-35 (Korean Patent No. 1072895)
HB48-59 (Korean Patent No. 1072895)
(2) Bovine serum (Gibco, 16170-078)
(3) Goat serum (Gibco, 16170-072)
(4) Skim milk (Difco, 232100)
(5) HBsAg-coated GENEDIA kit plate (GENEDIA Anti-HBs ELISA 3.0, GCMS, F1103)
(6) Tween 20 (Sigma, P1379)
(7) Goat anti-human IgG (Fc Specific, Peroxidase conjugated, Sigma, A0170)
(8) TMB Microwell peroxidase substrate (KPL, 50-76-03)
(9) Sulfuric acid ($H_2SO_4$, Riedel, 30743)
(10) Sodium chloride (Sigma, 53014)
(11) Acetic acid (Riedel, 27225)
(12) Sodium acetate trihydrate (Riedel, 25022)
(13) PBS (phosphate buffered saline) (Lonza, 17-516Q)
(14) BSA (bovine serum albumin) (Bovogen, BSA100)
(15) GENEDIA®, Anti-HBs ELISA 3.0 (GREEN CROSS CORP. MS, F1103)

Reagents used in the analysis were prepared by the following procedures.
(1) Tween 20 Having a Concentration of 10% (w/v):
10 g of original Tween 20 was added to 90 mL of distilled water and well-mixed.
(2) Heat of Inactivated Bovine Serum & Goat Serum
Bovine serum and goat serum dissolved at room temperature or 2° C. to 8° C. were heated at 56° C. for 30 minutes.
(3) Dilution Buffer (0.1% Skim Milk/0.05% Tween 20/10% Bovine Serum/90% PBS):
100 mL of heated and inactivated bovine serum, 1 g of skim milk and 5 mL of 10% Tween 20 were mixed and add PBS to make the solution 1 L. The mixture was well mixed so as not to have floating materials, and filtered by using 0.45 filter, and used.
(4) Secondary Antibody Complex Conjugate Solution (1:20,000):
5 μg of Goat anti-human IgG (specific to Fc and peroxidase conjugated) were added to 5 mL of heated and inactivated goat serum and well-mixed to prepare a solution. 1 mL of the prepared solution was well-mixed with 19 mL of heated and inactivated goat serum.

(5) Substrate Solution:

TMB peroxidase substrate A and TMB peroxidase substrate B were well-mixed at a ratio of 1:1.

(6) Solution for Stopping Reaction:

28 mL of sulfuric acid was slowly mixed in 972 mL of distilled water.

(7) Cleansing Solution:

2.722 g of sodium acetate trihyrate, 8.766 g of sodium chloride, 5 g of 10% Tween 20 were added 900 mL of distilled water, and controlled to have pH of 4.0 with original acetic acid and then made into a final volume of 1 L with distilled water and well-mixed.

(8) 1% (w/v) BSA/PBS:

10 g of BSA was dissolved in 1 L of PBS, and used.

(9) PBST 5 g of Tween 20 was added to 1 L of PBS and completely dissolved by a slow vortex without generating bubbles.

Diluent for samples, secondary antibodies, diluents for secondary antibody, and cleansing solutions of ELISA using 1% BSA/PBS as a diluent for sample, and those of Hepabig-Gene ELISA are shown in Table 1 below.

TABLE 1

Comparison of features between general ELISA and Hepabig-Gene ELISA

| | Diluent for samples | secondary antibodies | diluents for secondary antibody | cleansing solutions |
|---|---|---|---|---|
| general ELISA | 1% BSA/PBS | Anti-human IgG (Fab specific) | 1% BSA/PBS | PBST |
| Hepabig-Gene ELISA | 0.1% skim milk 10% Bovine serum 0.05 Tween 20 | Anti-human IgG (Fc specific) | 10% Goat Serum | Acetate (pH 4.0) 0.05 Tween 20 |

Analysis procedures for an antibody titer using GENEDIA® Anti-HBs ELISA 3.0 which is a diagnostic reagent for measuring an anti-HBs antibody titer were as follows. A negative standard solution, a standard solution, and a sample diluted by 10 to 25 times with the negative standard solution were added to a microwell plate in a diagnostic reagent. Then, a concentrated conjugate fluid was diluted 26 times with a diluent for conjugate, and the diluted concentrated conjugate fluid was added to the microwell plate in which the standard solution, the negative standard solution, and the sample were included, followed by gentle vortex to be well mixed with each other, and reacted at 37° C. for 1 to 60 minutes. After the reaction was completed, the obtained mixture was washed by using a concentrated cleansing solution in the diagnostic reagent, which was diluted 10 times with distilled water. A substrate solution in the diagnostic reagent was diluted 101 times with a buffer for substrate, and the diluted substrate solution was added to the washed microwell plate, followed by reaction at room temperature for 30 minutes. The reaction was stopped by adding a solution for stopping reaction in the diagnostic reagent.

Analysis procedures for an antibody titer using ELISA having 1% BSA/PBS as a diluent for sample were as follows. A recombinant hepatitis B virus surface antigen which was not treated with formalin, was coated on the microwell plate, followed by blocking using 1% BSA/PBS. Then, a standard solution and a human serum sample diluted 25 times with a diluent for sample (1% BSA/PBS) were added to the plate to induce a reaction. After the reaction was completed, the obtained mixture was washed with PBST, and was subjected to secondary reaction with goat anti-Human IgG Antibody (Fab Specific) and horseradish peroxidase conjugated, and washed with PBST again. After the secondary reaction was completed, TMB substrate solution was added to develop color, and the reaction was stopped by adding sulfuric acid solution thereto.

Analysis procedures for an antibody titer using Hepabig-Gene ELISA were as follows. A recombinant hepatitis B virus surface antigen which was not treated with formalin, was coated on the microwell plate, followed by blocking using 1% BSA/PBS. Then, a standard solution and a human serum sample diluted by 10 times with a diluent for sample (10% (w/v) bovine serum including 0.1% (w/v) Skim milk, 0.05% (w/v) Tween 20, and 0.05% (w/v) Proclin 300) were added to the microwell plate to induce a reaction. After the reaction was completed, the obtained mixture was washed with a cleansing solution, and was subjected to secondary reaction with goat anti-Human IgG Antibody (Fc Specific, horseradish peroxidase conjugated), and developed colors by adding TMB substrate.

In the primary analysis, background noise of Hepabig-Gene ELISA in human serum was confirmed by using serums taken from 19 patients suffering from hepatitis B (HBsAg (+)) which is generally known that the serums do not have anti-HBs antibody. First, it was confirmed that the anti-HBs antibody was not present in the serums of patients suffering from hepatitis B, using GENEDIA® Anti-HBs ELISA 3.0 diagnostic reagent (Table 2). When diluting the sample using 1% BSA/PBS, all of the 19 samples generated high background noise over 900 mIU/mL. However, in Hepabig-Gene ELISA, it was confirmed that all samples did not generate background noise below 100 mIU/mL.

TABLE 2 primary analysis results using serums taken from 19 patients suffering from hepatitis B

| | | anti-HBs | | |
|---|---|---|---|---|
| No. | HBsAg | Genedia | PBS/BSA | Hepabig-Gene ELISA |
| 1 | (+) | <250 | 1,014 | <100 |
| 2 | (+) | <250 | 1,023 | <100 |
| 3 | (+) | <250 | 970 | <100 |
| 4 | (+) | <250 | 1,189 | <100 |
| 5 | (+) | <250 | 1,691 | <100 |
| 6 | (+) | <250 | 1,734 | <100 |
| 7 | (+) | <250 | 1,757 | <100 |
| 8 | (+) | <250 | 1,662 | <100 |
| 9 | (+) | <250 | 967 | <100 |
| 10 | (+) | <250 | 478 | <100 |
| 11 | (+) | <250 | 974 | <100 |
| 12 | (+) | <250 | 1,770 | <100 |
| 13 | (+) | <250 | 2,341 | <100 |
| 14 | (+) | <250 | 2,701 | <100 |
| 15 | (+) | <250 | 2,644 | <100 |
| 16 | (+) | <250 | 1,228 | <100 |
| 17 | (+) | <250 | 1,266 | <100 |
| 18 | (+) | <250 | 1,358 | <100 |
| 19 | (+) | <250 | 1,305 | <100 |

In the secondary analysis, it was confirmed whether Hepabig-Gene ELISA is capable of normally measuring a titer without background noise even in human serum, using 21 serums taken from normal people which were not patients suffering from hepatitis B. In order to confirm whether the background noise is generated, GENEDIA® Anti-HBs ELISA 3.0 diagnostic reagent was used for comparison. In Hepabig-Gene ELISA, all of the 21 samples did not generate high background noise as the same as those of the serums using 1% BSA/PBS as the diluent for sample in the primary analysis. In addition, even though the result of the Hepabig-Gene ELISA was compared with the result of GENEDIA® Anti-HBs ELISA 3.0 diagnostic reagent, there was no difference in background noise (Table 3). In the secondary analysis, ELISA titer measurement using 1% BSA/PBS as the diluent for sample which was already confirmed that the background noise was high, was not used.

TABLE 3 secondary analysis results using serums taken from patients not suffering from hepatitis B

|     |       | Anti-HBs |                    |
|-----|-------|----------|--------------------|
| No. | HBsAg | Genedia  | Hepabig-Gene ELISA |
| 20  | (−)   | <100 (4) | <100 (14)          |
| 21  | (−)   | <100 (4) | <100 (3)           |
| 22  | (−)   | <100 (11)| <100 (39)          |
| 23  | (−)   | <100 (31)| <100 (20)          |
| 24  | (−)   | <100 (0) | <100 (2)           |
| 25  | (−)   | <100 (0) | <100 (0)           |
| 26  | (−)   | <100 (0) | <100 (2)           |
| 27  | (−)   | <100 (0) | <100 (13)          |
| 28  | (−)   | <100 (8) | <100 (1)           |
| 29  | (−)   | <100 (52)| 342                |
| 30  | (−)   | 135      | 355                |
| 31  | (−)   | 136      | 236                |
| 32  | (−)   | 377      | 402                |
| 33  | (−)   | 339      | 516                |
| 34  | (−)   | <100 (69)| 280                |
| 35  | (−)   | 225      | <100 (94)          |
| 36  | (−)   | 537      | 905                |
| 37  | (−)   | 1158     | 1833               |
| 38  | (−)   | >1500    | 2676               |
| 39  | (−)   | >1500    | 1474               |
| 40  | (−)   | >1500    | 1682               |

From the primary and secondary analysis results, it was confirmed that in the existing ELISA using 1% BSA/PBS as the diluent for sample in the primary and secondary analysis results, significantly high background noise over 900 mIU/mL was generated even though anti-HBs antibody titer was not present. However, in Hepabig-Gene ELISA, the background noise at a similar level to GENEDIA® Anti-HBs ELISA 3.0 diagnostic reagent which is commercially available, was generated. It means that high background noise generated at the time of using the existing anti-human IgG antibody as a secondary antibody is capable of being effectively controlled in Hepabig-Gene ELISA.

Example 2: Test for Comparison Between Titers Measured by Hepabig-Gene ELISA and AMC An object of Example 2 is to confirm correlation between titer measurement using Hepabig-Gene ELISA according to the present invention and anti-HBs antibody titer measurement (RIA (AMC) measurement) in the serum, using Anti-Hepatitis B Immunoglobulin national standards (KFDA Reference 08/026) of Ministry of Food and Drug Safety (MFDS). In the present Example, the national standard of (95.45 IU/vial, MFDS) hepatitis B immune human globulin was used.

Reagents used in the present Example and preparation procedures of the reagents were the same as those of Example 1, except for GENEDIA® Anti-HBs ELISA 3.0 diagnostic reagent.

Analysis procedures for an antibody titer using Hepabig-Gene ELISA were the same as Example 1.

In the RIA (AMC) measurement, the titer was measured by enzyme immuno assay (EIA) in which a surface antigen of hepatitis B virus is coated and reacted with a sample to be measured, and then, an enzyme such as peroxidase or alkaline phosphatase is conjugated with the surface antigen of hepatitis B virus like the existing anti-HBs antibody titer measurement as illustrated in FIG. 1A, or by radio-immuno assay (RIA) in which a radioactive isotope such as 125I is labeled on the surface antigen of the hepatitis B virus.

The analysis procedures using RIA (AMC) measurement were as follows. A negative control, a positive control, and a sample were added to test tubes, and bead coated with HBs antigen was added to each test tube, followed by oscillating reaction at room temperature or reaction at 45° C. for 90 minutes. After the reaction was completed, the bead was washed with distilled water 3 to 5 times, and 125I-HBs was added thereto, followed by oscillating reaction at room temperature or reaction at 45° C. for 90 minutes. After the reaction was completed, the bead was washed with distilled water 3 to 5 times. Then, within 24 hours after the washing, radioactivity in each test tube was measured for 1 minute by a gamma-ray instrument.

Preparation procedures of the analysis samples were as follows.

A negative control, a positive control, and a sample were added to test tubes, and bead coated with HBs antigen was added to each test tube, followed by oscillating reaction at room temperature or reaction at 45° C. for 90 minutes. After the reaction was completed, the bead was washed with distilled water 3 to 5 times, and 125I-HBs was added thereto, followed by oscillating reaction at room temperature or reaction at 45° C. for 90 minutes. After the reaction was completed, the bead was washed with distilled water 3 to 5 times. Then, within 24 hours after the washing, radioactivity in each test tube was measured for 1 minute by a gamma-ray instrument.

In the primary analysis, 30 blank samples were analyzed by Hepabig-Gene ELISA, and among the obtained analysis results, two results in which detection limit of Hepabig-Gene ELISA is less than 10 mIU/mL (<10 mIU/mL) were not included in the final results. 30 blind samples were analyzed by RIA (AMC) measurement, and among the obtained analysis results, two results in which detection limit of AMC measurement is less than 10 mIU/mL were not included in final results. Upon reviewing mean percent recoveries (% recovery: % RE) of each measurement, % RE of Hepabig-Gene ELISA was confirmed to be 956.0%, and % RE of RIA (AMC) measurement was confirmed to be 14712.9%, and analysis results were shown in Table 4 below.

TABLE 4 primary analysis results using Hepatitis B Immunoglobulin national standards (KFDA Reference 08/026)

|     | Theoretical        | Measured Titer (mIU/mL) |                       |
|-----|--------------------|-------------------------|-----------------------|
| No. | Titer (mIU/mL)     | GCC (% Recovery Rate)   | AMC (% Recovery Rate) |
| 1   | 50                 | 46 (92)                 | 86 (172)              |
| 2   | 50                 | 47 (94)                 | 96 (191)              |
| 3   | 250                | 241 (96)                | 314 (126)             |
| 4   | 250                | 250 (100)               | 331 (132)             |
| 5   | 500                | 452 (90)                | 795 (159)             |
| 6   | 500                | 518 (104)               | 756 (151)             |

TABLE 4-continued primary analysis results using Hepatitis B
Immunoglobulin national standards (KFDA Reference 08/026)

| | | | |
|---|---|---|---|
| 7 | 750 | 713 (95) | 1160 (155) |
| 8 | 750 | 842 (112) | 1120 (149) |
| 9 | 1000 | 839 (84) | 1530 (153) |
| 10 | 1000 | 957 (96) | 1520 (152) |
| 11 | 1250 | 1226 (98) | 1710 (137) |
| 12 | 1250 | 1163 (93) | 1770 (142) |
| 13 | 1500 | 1456 (97) | 2250 (150) |
| 14 | 1500 | 1435 (96) | 2270 (151) |
| 15 | 1750 | 1688 (96) | 2530 (145) |
| 16 | 1750 | 1603 (92) | 2540 (145) |
| 17 | 2000 | 2039 (102) | 2940 (147) |
| 18 | 2000 | 1809 (90) | 2660 (133) |
| 19 | 2250 | 2214 (98) | 3250 (144) |
| 20 | 2250 | 2077 (92) | 3530 (157) |
| 21 | 2500 | 2564 (103) | 3520 (141) |
| 22 | 2500 | 2330 (93) | 3490 (140) |
| 23 | 2750 | 2494 (91) | 3790 (138) |
| 24 | 2750 | 2529 (92) | 3830 (139) |
| 25 | 3000 | 2750 (92) | 4280 (143) |
| 26 | 3000 | 2895 (97) | 4230 (141) |
| 27 | 3500 | 3391 (97) | 4900 (143) |
| 28 | 3500 | 2823 (81) | 4750 (136) |

| | Sample Numbers | % Recovery Rate* (%, Mean ± SD) |
|---|---|---|
| GCC | 28 | 95 ± 6.0 |
| AMC | 28 | 147 ± 12.9 |

% Recovery Rate* = Measured Titer/Theoretical Titer × 100

In the secondary analysis, 28 blank samples were analyzed by Hepabig-Gene ELISA, and among the analysis results, four results in which detection limit of Hepabig-Gene ELISA is less than 10 mIU/mL were not included in the final results. 28 blank samples were analyzed by RIA (AMC) measurement, and among the obtained analysis results, four results in which detection limit of RIA (AMC) measurement is less than 10 mIU/mL were not included in final results. Upon reviewing mean percent recoveries (% recovery: % RE) of each measurement, % RE of Hepabig-Gene ELISA was confirmed to be 967.1%, and % RE of RIA (AMC) measurement was confirmed to be 14016.4%, and analysis results were shown in Table 5 below.

TABLE 5 secondary analysis results using Hepatitis B
Immunoglobulin national standards (KFDA Reference 08/026)

| | Theoretical | Measured Titer (mIU/mL) | |
|---|---|---|---|
| No. | Titer (mIU/mL) | GCC (% Recovery Rate) | AMC (% Recovery Rate) |
| 1 | 27 | 28 (103) | 43 (157) |
| 2 | 27 | 25 (92) | 44 (163) |
| 3 | 35 | 31 (89) | 57 (163) |
| 4 | 35 | 31 (89) | 53 (150) |
| 5 | 55 | 58 (106) | 83 (151) |
| 6 | 55 | 55 (101) | 88 (161) |
| 7 | 109 | 105 (96) | 183 (168) |
| 8 | 109 | 103 (94) | 173 (158) |
| 9 | 218 | 220 (101) | 255 (117) |
| 10 | 218 | 218 (100) | 245 (112) |
| 11 | 350 | 338 (97) | 427 (122) |
| 12 | 350 | 321 (92) | 417 (119) |
| 13 | 438 | 452 (103) | 555 (127) |
| 14 | 438 | 408 (93) | 546 (125) |
| 15 | 700 | 763 (109) | 965 (138) |
| 16 | 700 | 708 (101) | 915 (131) |
| 17 | 875 | 907 (104) | 1140 (130) |
| 18 | 875 | 869 (99) | 1160 (133) |

TABLE 5-continued secondary analysis results using Hepatitis B
Immunoglobulin national standards (KFDA Reference 08/026)

| | | | |
|---|---|---|---|
| 19 | 1400 | 1354 (97) | 2150 (154) |
| 20 | 1400 | 1199 (86) | 1870 (134) |
| 21 | 1750 | 1503 (86) | 2280 (130) |
| 22 | 1750 | 1396 (80) | 2410 (138) |
| 23 | 3500 | 3329 (95) | 5090 (145) |
| 24 | 3500 | 3327 (95) | 4830 (138) |

| | Sample Numbers | % Recovery Rate* (%, Mean ± SD) |
|---|---|---|
| GCC | 24 | 96 ± 7.1 |
| AMC | 24 | 140 ± 16.4 |

% Recovery Rate* = Measured Titer/Theoretical Titer × 100

2-Sample t-test with respect to the primary and secondary analysis results (those are different in view of preparation institution) was conducted by using % RE of each measurement (95% confidence level). Significance probability (P-value) on the primary analysis results and the secondary analysis results of Hepabig-Gene ELISA was 0.565, and significance probability (P-value) on the primary analysis results and the secondary analysis results of AMC measurement was 0.112. Two significance probabilities (P-values) on the primary and secondary analysis results were 0.05 or more, and accordingly, it was regarded that there was no difference between the primary analysis results and the secondary analysis results, and the following analysis for results was conducted by using final analysis results including total primary and secondary results (Table 6).

TABLE 6 final analysis results using Hepatitis B
Immunoglobulin national standards (KFDA Reference 08/026)

| | Theoretical | Measured Titer (mIU/mL) | |
|---|---|---|---|
| No. | Titer (mIU/mL) | GCC (% Recovery Rate) | AMC (% Recovery Rate) |
| 1 (secondary) | 27 | 28 (103) | 43 (157) |
| 2 (secondary) | 27 | 25 (92) | 44 (163) |
| 3 (secondary) | 35 | 31 (89) | 57 (163) |
| 4 (secondary) | 35 | 31 (89) | 53 (150) |
| 5 (primary) | 50 | 46 (92) | 86 (172) |
| 6 (primary) | 50 | 47 (94) | 96 (191) |
| 7 (secondary) | 55 | 58 (106) | 83 (151) |
| 8 (secondary) | 55 | 55 (101) | 88 (161) |
| 9 (secondary) | 109 | 105 (96) | 183 (168) |
| 10 (secondary) | 109 | 103 (94) | 173 (158) |
| 11 (secondary) | 218 | 220 (101) | 255 (117) |
| 12 (secondary) | 218 | 218 (100) | 245 (112) |
| 13 (primary) | 250 | 241 (96) | 314 (126) |
| 14 (primary) | 250 | 250 (100) | 331 (132) |
| 15 (secondary) | 350 | 338 (97) | 427 (122) |
| 16 (secondary) | 350 | 321 (92) | 417 (119) |
| 17 (secondary) | 438 | 452 (103) | 555 (127) |
| 18 (secondary) | 438 | 408 (93) | 546 (125) |
| 19 (primary) | 500 | 452 (90) | 795 (159) |
| 20 (primary) | 500 | 518 (104) | 756 (151) |
| 21 (secondary) | 700 | 763 (109) | 965 (138) |
| 22 (secondary) | 700 | 708 (101) | 915 (131) |
| 23 (primary) | 750 | 713 (95) | 1160 (155) |
| 24 (primary) | 750 | 842 (112) | 1120 (149) |
| 25 (secondary) | 875 | 907 (104) | 1140 (130) |
| 26 (secondary) | 875 | 869 (99) | 1160 (133) |
| 27 (primary) | 1000 | 839 (84) | 1530 (153) |
| 28 (primary) | 1000 | 957 (96) | 1520 (152) |
| 29 (primary) | 1250 | 1226 (98) | 1710 (137) |
| 30 (primary) | 1250 | 1163 (93) | 1770 (142) |
| 31 (secondary) | 1400 | 1354 (97) | 2150 (154) |

TABLE 6-continued final analysis results using Hepatitis B
Immunoglobulin national standards (KFDA Reference 08/026)

| | | | |
|---|---|---|---|
| 32 (secondary) | 1400 | 1199 (86) | 1870 (134) |
| 33 (primary) | 1500 | 1456 (97) | 2250 (150) |
| 34 (primary) | 1500 | 1435 (96) | 2270 (151) |
| 35 (primary) | 1750 | 1688 (96) | 2530 (145) |
| 36 (primary) | 1750 | 1603 (92) | 2540 (145) |
| 37 (secondary) | 1750 | 1503 (86) | 2280 (130) |
| 38 (secondary) | 1750 | 1396 (80) | 2410 (138) |
| 39 (primary) | 2000 | 2039 (102) | 2940 (147) |
| 40 (primary) | 2000 | 1809 (90) | 2660 (133) |
| 41 (primary) | 2250 | 2214 (98) | 3250 (144) |
| 42 (primary) | 2250 | 2077 (92) | 3530 (157) |
| 43 (primary) | 2500 | 2564 (103) | 3520 (141) |
| 44 (primary) | 2500 | 2330 (93) | 3490 (140) |
| 45 (primary) | 2750 | 2494 (91) | 3790 (138) |
| 46 (primary) | 2750 | 2529 (92) | 3830 (139) |
| 47 (primary) | 3000 | 2750 (92) | 4280 (143) |
| 48 (primary) | 3000 | 2895 (97) | 4230 (141) |
| 49 (primary) | 3500 | 3391 (97) | 4900 (143) |
| 50 (primary) | 3500 | 2823 (81) | 4750 (136) |
| 51 (secondary) | 3500 | 3329 (95) | 5090 (145) |
| 52 (secondary) | 3500 | 3327 (95) | 4830 (138) |

| | Sample Numbers | % Recovery Rate* (%, Mean ± SD) |
|---|---|---|
| GCC | 52 | 96 ± 6.5 |
| AMC | 52 | 144 ± 14.5 |

% Recovery Rate* = Measured Titer/Theoretical Titer × 100

Figure 4:
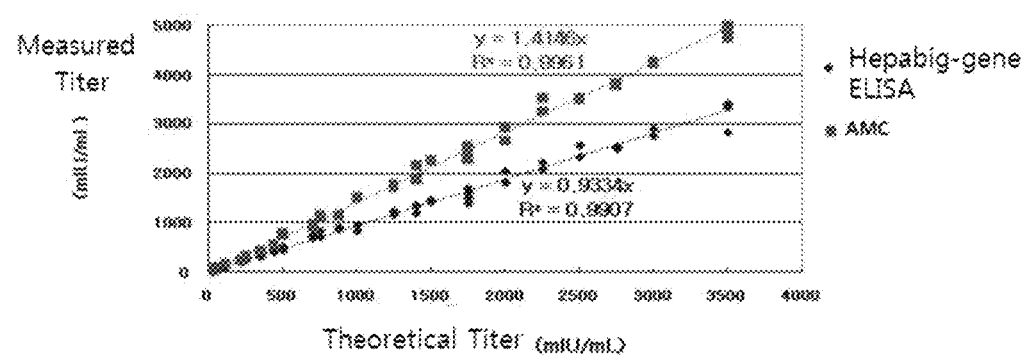
FIG. 4 is a graph illustrating results of linear regression analysis of final analysis results of experiments for measuring an antibody titer using Hepabig-Gene ELISA and RIA (AMC).

Upon reviewing mean percent recoveries (% recovery: % RE) of each measurement in the final analysis results, % RE of Hepabig-Gene ELISA was confirmed to be 966.5%, and % RE of RIA (AMC) measurement was confirmed to be 14414.8%. As results from linear regression analysis using excel, % RE of Hepabig-Gene ELISA was 93.3% as compared to a theoretical titer of the national standard, and % RE of RIA (AMC) measurement was 141.5% as compared to the theoretical titer of the national standard (Table 6). In addition, a value of $R^2$ was also 0.99 or more, which may be appreciated that Hepabig-Gene ELISA has significantly high explanation power of linear regression analysis model (FIG. 4).

Figure 5:
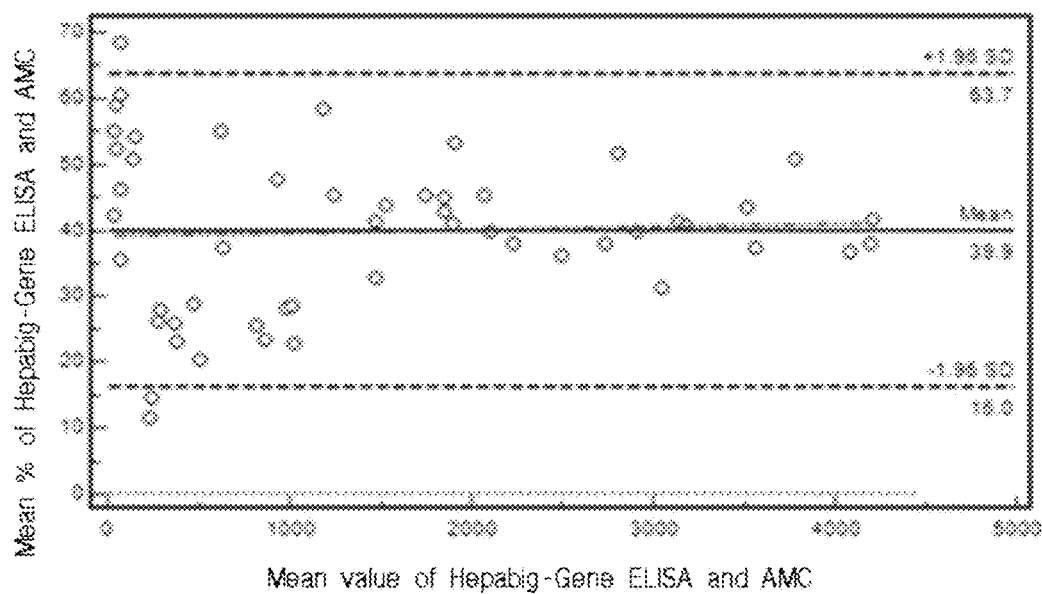
FIG. 5 is a graph illustrating Bland & Altman plot of RIA (AMC) analysis results and Hepabig-Gene ELISA analysis results.

Equivalence of two measurements was evaluated by Bland & Altman plots. These plots were distributed in 95% confidence interval (1.96SD); however, it was confirmed that a mean value of y of the plots was 39.9% (FIG. 5), and a relationship as the same as the following Equation was established.

Results of RIA (AMC) measurement−Results of
Hepabig-Gene ELISA=0.399 Average (Mean)
between the measurement results That is, the difference in two measurement results was 39.9% of the mean on two measurement results. From these results, it was confirmed that two measurements and analysis results were not equal to each other.

As a correlation coefficient, Pearson correlation coefficient (95% confidence level, JMP v8.0) was used for evaluation. The Pearson correlation coefficient was 0.996 (significant probability (P-value) is 0.000), and it could be appreciated that the analysis results of two test measurements have strong positive correlation.

Regression analysis was conducted by putting titer analysis values of Hepabig-Gene ELISA on X-axis, and titer analysis values of RIA (AMC) measurement of department of nuclear medicine at Asan Medical Center on Y-axis. As a result of the regression analysis, the following linear regression equation was obtained and significant possibility (P-value) with respect to the coefficient was 0.000, and highly significant at a significant level of 0.05.

RIA (AMC)=1.51 Hepabig-Gene ELISA [linear regression equation

From these results, it could be appreciated that 500 mIU/mL which is the analysis result of the RIA (AMC) measurement when diluting the national standards using the existing diluent for sample was the same as 331 mIU/mL, a mean value of the analysis result of Hepabig-Gene ELISA.

That is, from the experimental results of the present Example, it could be confirmed that Hepabig-Gene ELISA properly evaluated the national standard (93.3% RE in the linear regression analysis result); however, RIA (AMC) measurement highly evaluated the national standard by 1.4 times (141.5% RE in the linear regression analysis result). It was confirmed that the analysis results of two measurements had strong positive correlation coefficient (evaluated by Pearson correlation coefficient), and the measurement results of RIA (AMC) were highly evaluated by 1.51 times as compared to those of Hepabig-Gene ELISA. In addition, it was confirmed that the antibody titer measurement by Hepabig-Gene ELISA had the same measurement precision as the existing measurement, and was capable of more accurately measuring an antibody amount as compared to the existing measurement.

Example 3: Test for Comparison Between Titers Measured by Hepabig-Gene ELISA and AMC An object of the present Example is to compare and analyze anti-HBs titer measurement values among four kinds of anti-HBs titer measurements such as Hepabig-Gene ELISA, ELISA using 1% BSA/PBS as a diluent for sample, RIA (AMC), and GENEDIA® Anti-HBs ELISA 3.0 diagnostic reagent, in 156 serums of patients to which hepatitis B immunoglobulin (HBIG) are administered in order to prevent recurrence of hepatitis B after receiving the liver plant due to hepatitis B.

Reagents used in Hepabig-Gene ELISA, ELISA using 1% BSA/PBS as a diluent for sample, RIA (AMC), and GENEDIA® Anti-HBs ELISA 3.0 diagnostic reagent, and preparation procedures of the reagents were the same as those of Examples 1 and 2. In addition, analysis methods of Hepabig-Gene ELISA, ELISA using 1% BSA/PBS as a diluent for sample, and GENEDIA® Anti-HBs ELISA 3.0 diagnostic reagent, were the same as Example 1, and analysis methods of RIA (AMC) was the same as Example 2.

Figure 6:
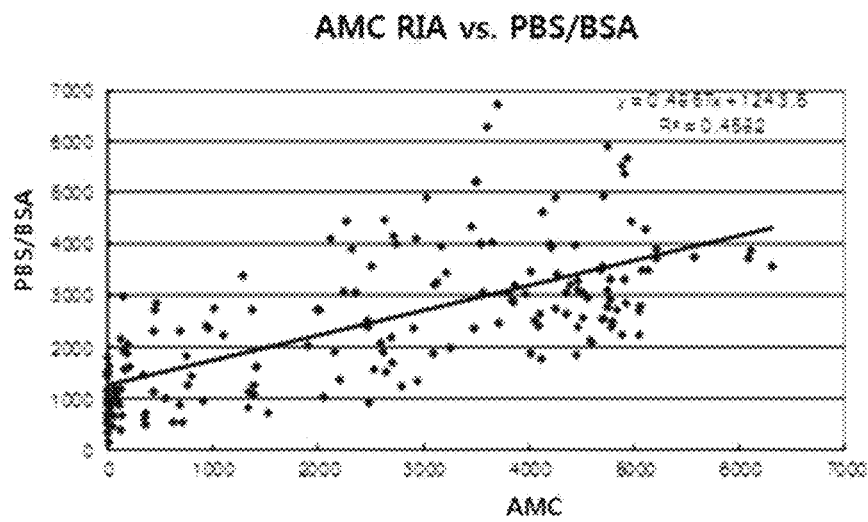
FIG. 6 is a graph illustrating comparison between ELISA titer measurement method using the existing 1% BSA/PBS as a diluent for sample and RIA (ASM) analysis results.

When comparing the existing ELISA titer measurement using 1% BSA/PBS as a diluent for sample with RIA (AMC), the samples having a low titer close to 0 in the RIA (AMC) generated high background noise up to the maximum of 2,000 mIU/mL in ELISA titer measurement using 1% BSA/PBS as a diluent for sample, as illustrated in FIG. 6. It is similar to the results of Example 1. In addition, the correlation between two methods was low as $R^2$=0.4582, and a slope of the regression trend line was 0.4857, and accordingly, it could be appreciated that the same samples were highly measured in the RIA (AMC) as compared to the ELISA titer measurement using 1% BSA/PBS.

Figure 7:
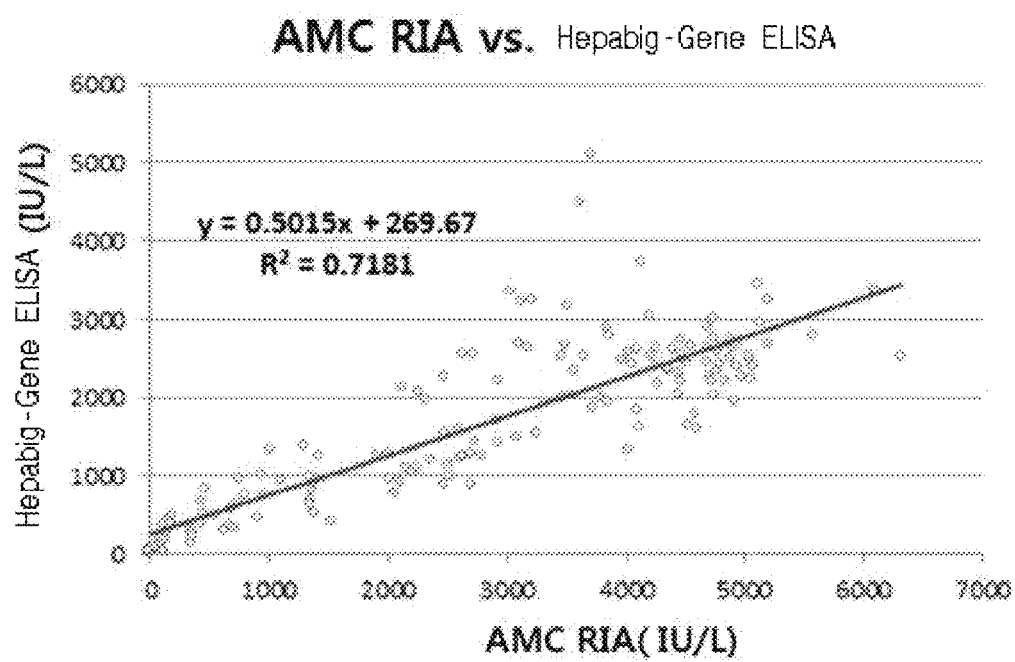
FIG. 7 is a graph illustrating comparison between the Hepabig-Gene ELISA analysis results and RIA (ASM) analysis results.

Meanwhile, when comparing Hepabig-Gene ELISA with RIA (AMC), it was confirmed that the background noise was effectively removed by Hepabig-Gene ELISA, and $R^2$ was 0.7181, which was confirmed that the correlation with the RIA (AMC) was improved as compared to the method using 1% BSA/PBS, as illustrated in FIG. 7. However, the slope of the regression trend line between two methods was 0.5015, which was confirmed that the samples were highly measured in RIA (AMC) method as compared to Hepabig-Gene ELISA, similar to the comparison between the RIA (AMC) and the method using 1% BSA/PBS. It may be appreciated that these results were significantly similar to those of Example 2.

When comparing Hepabig-Gene ELISA with GENEDIA® Anti-HBs ELISA 3.0 diagnostic reagent, $R^2$ was 0.8627, which had high correlation between two methods, and the slope of the regression trend line between two methods was 1.0068. That is, it was confirmed that the measurement values between two methods were almost the same as each other, as illustrated in FIG. 8.

Figure 8:
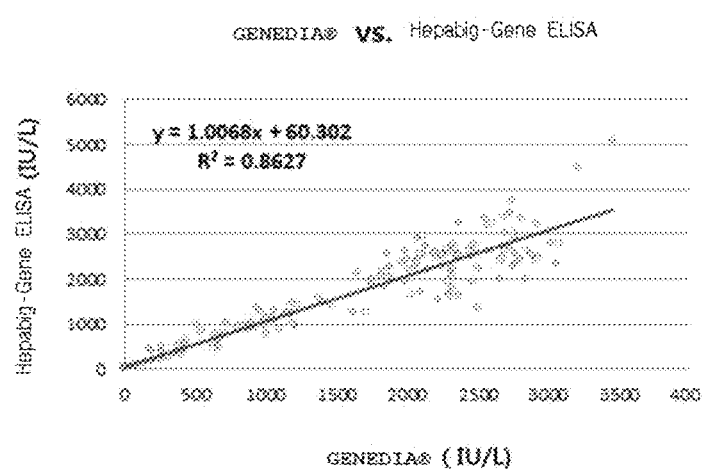
FIG. 8 is a graph illustrating comparison between the Hepabig-Gene ELISA analysis results and GENEDIA® Anti-HBs ELISA 3.0 diagnostic reagent analysis results.

As illustrated in FIGS. 6 to 8, Hepabig-Gene ELISA effectively reduced high background noise in human serum according to the existing method using 1% BSA/PBS, and had high correlation with commercially available RIA and GENEDIA® Anti-HBs ELISA 3.0 diagnostic reagent. Particularly, it was confirmed that the measurement results of Hepabig-Gene ELISA were almost the same as those of GENEDIA® Anti-HBs ELISA 3.0 diagnostic reagent.

Example 4: Measurement for Anti-HBs Antibody Titer in Rat Serum Using GC1102

The present Example was conducted to confirm whether the titer measurement using Hepabig-Gene ELISA according to the present invention for measuring the titer of the anti-hepatitis B virus surface (anti-HBs) antibody in human serum, is possible to measure anti-HBs antibody titer (anti-HBs antibody titer of GC1102, GC1102 mixed in IV-Hepabig injection, and GC1102 mixed in IV-Globulin S injection) in rat serum.

Standards and samples used in the present Example were as follows.

(1) Standards: Standards of Hepabig-Gene ELISA, anti-HBs titer of 10,500 IU/mL.

(2) GC1102: anti-HBs monoclonal antibody, anti-HBs titer of 10,500 IU/mL.

(3) IV-Hepabig injection: intravenous Hepabig injection of 10 mL, anti-HBs titer of 270.5 IU/mL.

(4) IV-Globulin S injection: IV-Globulin S injection of 10 mL, anti-HBs titer of 2.2 IU/mL.

The reagents used in the present Example were the same as those of the Examples above, and the reagents including the diluent for sample, the diluent for conjugate, the cleansing solution, and the like, were also prepared by the same method as Examples above. Standard solutions were prepared by diluting GC1102 titer standards with dilution buffer and controlling a concentration to be 0, 10, 50, 100, 150, 500, or 1000 IU/mL, and a standard curve was obtained.

QC samples of GC1102 (10,500 IU/mL) and IV-Hepabig injection (270.5 IU/mL, GREEN CROSS CORP.) were prepared by diluting GC1102 with rat serum and controlling concentrations to be 200, 1000, 4000, 8000 mIU/mL, respectively.

QC samples of GC1102 and IV-globulin S injection (Green Cross Corp.) were prepared as mixtures by controlling protein concentration (mg/mL) of the IV-globulin S injection to be the same as the protein concentration of IV-Hepabig injection with buffer, and mixing so as to have the same anti-HBs antibody titer as the IV-Hepabig injection. The prepared mixtures were diluted with rat serum and controlled to have concentrations of 200, 1000, 4000, 8000 mIU/mL, respectively.

Analysis of anti-HBs antibody titer of IV-Hepabig injection using Hepabig-Gene ELISA was conducted to confirm whether about 270.5 IU/mL which is the anti-HBs antibody titer defined in the representative report on Lot. 150H8028 of IV-Hepabig injection was measured in analysis using Hepabig-Gene ELISA. As the sample, IV-Hepabig injections diluted by 800 times, 1,600 times, 3,200 times, and 6,400 times with diluent for sample of Hepabig-Gene ELISA, were used.

Evaluating accuracy was conducted by repeating the test six times per concentration, and spiking 4 concentrations within an analysis range. In evaluating accuracy, samples were evaluated by % recovery (% RE) and it was confirmed whether % RE was measured within 80 to 120%.

Evaluating precision was conducted by repeating the test six times per concentration, and spiking 4 concentrations within analysis range. In evaluating precision, samples were evaluated by % relative standard deviation (% RSD), and it was confirmed whether % RSD was measured within 15%. Further, intra-assay precision and inter-assay precision were evaluated, wherein the intra-assay precision was evaluated by confirming whether % RSD among results obtained by repeating the test twice with respect to one standard, is within 15%, and the inter-assay precision was evaluated by confirming whether % RSD among results obtained by repeating the test three times per day, is within 15%.

In evaluating selectivity, it was confirmed that there was no interference effect of a biological medium by using 8 rat serums. % RE was confirmed by spiking GC1102 (50 mIU/mL) in 8 rat serums and absence of an interference effect was also confirmed.

Other test methods used in the present Example were the same as those of Hepabig-Gene ELISA of Example 1.

1) Analysis of Anti-HBs Antibody Titer of IV-Hepabig Injection Using Hepabig-Gene ELISA Anti-HBs antibody titer of IV-Hepabig injection diluted 800 times, 1,600 times, 3,200 times, 6,400 times with the diluent for sample of the Hepabig-Gene ELISA, was measured by using Hepabig-Gene ELISA. The analysis result was 276.0 IU/mL (% RSD of 4.7%), which was measured as the same as the result of representative report of IV-Hepabig injection, 270.5 IU/mL, within standard deviation, and accordingly, it was confirmed that Hepabig-Gene ELISA was usable for measuring titer in vitro such as a shipping test of the anti-HBs antibody of plasma-derived HBIG preparation, for example, IV-Hepabig injection (Table 7).

TABLE 7

| Dilution Rate | Observed Results (mIU/mL) | Adjusted Results (IU/mL) | % Recovery of Spiking Sample |
|---|---|---|---|
| 800 | 328.4 | 262.7 | 115.3 |
| 1,600 | 169.7 | 271.5 | 105.1 |
| 3,200 | 86.3 | 276.0 | 95.3 |
| 6,400 | 45.9 | 293.6 | 98.4 |
| Mean | | 276.0 | |
| SD | | 13.0 | |
| % RSD | | 4.7 | |

2) Measurement of GC1102 Antibody Titer in Rat Serum Using Hepabig-Gene ELISA

In order to measure GC1102 antibody titer in rat serum using Hepabig-Gene ELISA, QC samples obtained by spiking GC1102 (8,000, 4,000, 1,000, and 200 mIU/mL) in rat serum, were analyzed by Hepabig-Gene ELISA 1.1, and then accuracy, intra-assay precision, and inter-assay precision were confirmed. The test was repeated six times by including the spiking of GC1102 (200 mIU/mL, 1,000 mIU/mL, 4,000 mIU/mL, and 8,000 mIU/mL) in rat serum. % RE was 88.8 to 107.5%, the intra-assay precision (% RSD) was within 13.7%, and inter-assay precision (% RSD) was within 11.0%, which was confirmed that the anti-HBs titer of GC1102 was capable of being measured by using Hepabig-Gene ELISA even in the rat serum as well as human serum (Table 8).

TABLE 8

GC1102 spiking test results of in rat serum by using Hepabig-Gene ELISA

| Conc. (mIU/mL) | Run | Results | Intra-Assay Mean | SD | % RSD | % RE | Inter-Assay Mean | SD | % RSD | % RE |
|---|---|---|---|---|---|---|---|---|---|---|
| 8,000 | 1st | 8,980 8,173 | 8,577 | 570.6 | 6.7 | 107.2 | 8,081 | 890.3 | 11.0 | 101.0 |
|  | 2nd | 7,863 6,472 | 7,168 | 983.6 | 13.7 | 89.6 |  |  |  |  |
|  | 3rd | 8,212 8,783 | 8,498 | 403.8 | 4.8 | 106.2 |  |  |  |  |
| 4,000 | 1st | 3,977 3,786 | 3,882 | 135.1 | 3.5 | 97.0 | 3,749 | 170.6 | 4.5 | 93.7 |
|  | 2nd | 3,606 3,498 | 3,552 | 76.4 | 2.1 | 88.8 |  |  |  |  |
|  | 3rd | 3,321 3,808 | 3,815 | 9.2 | 0.2 | 95.4 |  |  |  |  |
| 1,000 | 1st | 887 890 | 889 | 2.1 | 0.2 | 88.9 | 940 | 40.5 | 4.3 | 94.0 |
|  | 2nd | 972 961 | 967 | 7.8 | 0.8 | 96.7 |  |  |  |  |
|  | 3rd | 952 976 | 964 | 17.0 | 1.8 | 96.4 |  |  |  |  |
| 200 | 1st | 209 197 | 203 | 8.5 | 4.2 | 101.5 | 206 | 9.2 | 4.5 | 102.8 |
|  | 2nd | 215 215 | 215 | 0.0 | 0.0 | 107.5 |  |  |  |  |
|  | 3rd | 193 204 | 199 | 7.8 | 3.9 | 99.3 |  |  |  |  |

% RSD = SD/Mean × 100,
% RE = Mean/Conc. × 100,
Bold = % RE <80 or % RE >120,
Italic = % RSD >15

3) Measurement of Antibody Titer of IV-Hepabig Injection in Rat Serum Using Hepabig-Gene ELISA QC samples obtained by spiking IV-Hepabig injection (8,000, 4,000, 1,000, and 200 mIU/mL) in rat serum, were analyzed by Hepabig-Gene ELISA, and then accuracy, intra-assay precision, and inter-assay precision were confirmed. The test was repeated six times by including the spiking of IV-Hepabig injection (200 mIU/mL, 1,000 mIU/mL, 4,000 mIU/mL, and 8,000 mIU/mL) in rat serum. % RE was 92.2 to 111.8%, the intra-assay precision (% RSD) was within 11.4%, and inter-assay precision (% RSD) was within 6.8%, which was confirmed that the anti-HBs titer of preparations such as plasma-derived HBIG was capable of being measured by using Hepabig-Gene ELISA even in the rat serum (Table 9).

TABLE 9

Experimental results on antibody titer of IV-Hepabig injection in rat serum using Hepabig-Gene ELISA

| Conc. (mIU/mL) | Run | Results | Intra-Assay Mean | SD | % RSD | % RE | Inter-Assay Mean | SD | % RSD | % RE |
|---|---|---|---|---|---|---|---|---|---|---|
| 8,000 | 1st | 9,171 7,804 | 8,488 | 966.6 | 11.4 | 106.1 | 8,255 | 333.6 | 6.5 | 103.2 |
|  | 2nd | 7,713 8,052 | 7,883 | 239.7 | 3.0 | 98.5 |  |  |  |  |
|  | 3rd | 8,157 8,330 | 8,394 | 89.8 | 1.1 | 104.9 |  |  |  |  |
| 4,000 | 1st | 4,393 4,185 | 4,289 | 147.1 | 3.4 | 107.2 | 3,965 | 270.8 | 6.8 | 99.1 |
|  | 2nd | 3,703 3,934 | 3,819 | 163.3 | 4.3 | 95.5 |  |  |  |  |
|  | 3rd | 3,760 3,812 | 3,786 | 36.8 | 1.0 | 94.7 |  |  |  |  |
| 1,000 | 1st | 1,016 978 | 997 | *26.9* | 3.7 | 99.7 | 976 | 44.6 | 4.6 | 97.6 |
|  | 2nd | 1,002 1,016 | 1,009 | 9.9 | 1.0 | 100.9 |  |  |  |  |
|  | 3rd | 913 930 | 922 | 12.0 | 1.3 | 92.2 |  |  |  |  |
| 200 | 1st | 220 209 | 215 | 7.8 | 3.6 | 107.3 | 214 | 9.4 | 4.4 | 107.1 |
|  | 2nd | 225 222 | 224 | 2.1 | 0.9 | 111.8 |  |  |  |  |

TABLE 9-continued

Experimental results on antibody titer of
IV-Hepabig injection in rat serum using Hepabig-Gene ELISA

| Conc. | | | Intra-Assay | | | | Inter-Assay | | | |
|---|---|---|---|---|---|---|---|---|---|---|
| (mIU/mL) | Run | Results | Mean | SD | % RSD | % RE | Mean | SD | % RSD | % RE |
| | 3rd | 202 | *205* | *3.5* | 1.7 | 102.3 | | | | |
| | | 207 | | | | | | | | |

% RSD = SD/Mean × 100,
% RE = Mean/Conc. × 100,
Bold = % RE <80 or % RE >120,
Italic = % RSD >15

4) Measurement of Antibody Titer of GC1102+IV-Globulin S Injection in Rat Serum Using Hepabig-Gene ELISA QC samples obtained by spiking mixtures containing GC1102 and IV-globulin S injection at a ratio of 1:24 (8,000, 4,000, 1,000, and 200 mIU/mL) in rat serum, were analyzed by Hepabig-Gene ELISA, and then accuracy, intra-assay precision, and inter-assay precision were confirmed. The test was repeated six times by including the spiking of IV-Hepabig injection (200 mIU/mL, 1,000 mIU/mL, 4,000 mIU/mL, and 8,000 mIU/mL) in rat serum. % RE was 83.8 to 102.8%, the intra-assay precision (% RSD) was within 7.5%, and inter-assay precision (% RSD) was within 7.8%, which was confirmed that the anti-HBs titer was capable of being measured by using Hepabig-Gene ELISA even in the globulin preparation mixture containing GC1102 and IV-globulin S injection (Table 10).

5) Evaluation of Selectivity

In order to confirm selectivity, 8 rat serums and spiked samples obtained by spiking GC1102 (500 mIU/mL) in rat serum were analyzed by using Hepabig-Gene ELISA. When analyzing all of the 8 rat serums by using Hepabig-Gene ELISA, anti-HBs antibody titer was negatively measured in all of the 8 rat serums, and when analyzing all of the spiked samples obtained by spiking GC1102 (500 mIU/mL) in rat serum, % RE was 96.0 to 106.2%, which was confirmed that there was no interference effect with respect to other components in the rat serum (Table 11).

TABLE 11

Results on evaluation of selectivity by using Hepabig-Gene ELISA

| Sample | Blank Sample | Spiked Sample | AR % |
|---|---|---|---|
| A | <100 | 492 | 98.4 |
| B | <100 | 481 | 96.0 |

TABLE 10

Results of measuring antibody titer of
GC1102 + IV-globulin S injection in rat serum using
Hepabig-Gene ELISA

| Conc. (mIU/mL) | Run | Results | Intra-Assay | | | | Inter-Assay | | | |
|---|---|---|---|---|---|---|---|---|---|---|
| | | | Mean | SD | % RSD | % RE | Mean | SD | % RSD | % RE |
| 8,000 | 1st | 6,665 6,971 | 6,818 | 216.4 | 3.2 | 85.2 | 7,451 | 583.7 | 7.8 | 93.1 |
| | 2nd | 7,297 8,119 | 7,708 | 581.2 | 7.5 | 96.4 | | | | |
| | 3rd | 7,602 8,053 | 7,828 | 318.9 | 4.1 | 97.8 | | | | |
| 4,000 | 1st | 3,809 3,746 | 3,778 | 44.5 | 1.2 | 94.4 | 3,585 | 197.9 | *5.5* | 89.6 |
| | 2nd | 3,342 3,363 | 3,353 | 14.8 | 0.4 | 83.8 | | | | |
| | 3rd | 3,560 3,689 | 3,625 | 91.2 | 2.5 | 90.6 | | | | |
| 1,000 | 1st | 894 923 | 909 | 20.5 | 2.3 | 90.9 | 894 | 18.2 | 2.0 | 89.4 |
| | 2nd | 876 884 | 680 | 5.7 | 0.6 | 88.0 | | | | |
| | 3rd | 880 908 | 894 | 19.8 | 2.2 | 89.4 | | | | |
| 200 | 1st | 182 183 | 183 | 0.7 | 0.4 | 91.3 | 194 | 11.1 | 5.7 | 96.8 |
| | 2nd | 208 203 | 206 | 3.5 | 1.7 | 102.8 | | | | |
| | 3rd | 187 199 | 193 | 8.5 | 4.4 | 96.5 | | | | |

% RSD = SD/Mean × 100,
% RE = Mean/Conc. × 100,
Bold = % RE <80 or % RE >120,
Italic = % RSD >15

TABLE 11-continued

Results on evaluation of selectivity by using Hepabig-Gene ELISA

| Sample | Blank Sample | Spiked Sample | AR % |
|---|---|---|---|
| C | <100 | 491 | 97.9 |
| D | <100 | 517 | 103.4 |
| E | <100 | 483 | 96.6 |
| F | <100 | 491 | 98.3 |
| G | <100 | 510 | 102.0 |
| H | <100 | 531 | 106.2 |

Even in cases using HB48-33, HB48-35, and HB48-59 (Korean Patent No. 1072895) which are other anti-HBs antibodies other than GC1102, it could be confirmed that the titer of all antibodies was capable of being accurately measured by Hepabig-Gene ELISA, which is similar to GC1102, as compared to the existing method.

The present invention has been described in detail based on particular features thereof, and it is obvious to those skilled in the art that these specific technologies are merely preferable embodiments, and accordingly, the scope of the present invention is not limited to the embodiments. Therefore, the substantial scope of the present invention is defined by the accompanying claims and equivalent thereof.

INDUSTRIAL APPLICABILITY

The kit for measuring the titer of the Fc-containing protein according to the present invention may overcome limitation in which the titer of the specific Fc-containing protein such as a human antibody, a humanized antibody, or a human Fc-fusion protein is not capable of being accurately measured due to a number of non-specific antibodies present in human plasma or serum in the existing kit for measuring the titer using an enzyme immunoassay (EIA) utilizing coating of specific antigens or functional groups, and may measure the titer of the a protein comprising human Fc in the human plasma or serum while maintaining high precision among test subjects.

In particular, the existing titer measurement of a protein comprising human Fc, in particular, a human antibody or a humanized antibody, has a measurable range from 10 mIU/mL to the maximum of 1,000 mIU/mL. However, the titer measurement using the kit for measuring the titer of the a protein comprising human Fc according to the present invention, has a much broader measurement range from 100 mIU/mL to the maximum of 10,000 mIU/mL.

Further, according to the present invention, the titer is capable of being measured with high precision even in measuring the titer of antibodies or Fc-containing protein derived from specific animal species similar to the present invention, in plasma or serum of the same animal species.

The invention claimed is:

1. A kit for measuring a titer of a protein comprising a human Fc:
    (a) a mixture including 5 to 100 (w/v) % bovine serum, 0.05 to 0.2% (w/v) skim milk, and a non-ionic surfactant for dilution of a sample comprising the protein comprising a human Fc;
    (b) a diluent for conjugate including an 10% (w/v) goat serum; and
    (c) a cleansing solution including sodium acetate, sodium chloride, and a non-ionic surfactant.

2. The kit of claim 1, wherein the non-ionic surfactant of (a) has a concentration of 0.025 to 0.1% (w/v).

3. The kit of claim 1, wherein the mixture of (a) further includes a preservative.

4. The kit of claim 3, wherein the preservative is Proclin 300.

5. The kit of claim 3, wherein the preservative has a concentration of 0.025 to 0.1% (w/v).

6. The kit of claim 1, wherein the goat serum of (b) includes goat anti-human IgG.

7. The kit of claim 6, wherein the goat anti-human IgG is specific to human Fc.

8. The kit of claim 1, wherein the protein comprising a human Fc is one or more selected from the group consisting of a human antibody, a humanized antibody, and a fusion protein containing human Fc.

9. The kit of claim 1, wherein the sodium acetate of the cleansing solution of (c) has a concentration of 10 to 40 mM.

10. The kit of claim 1, wherein the sodium chloride of the cleansing solution of (c) has a concentration of 75 to 300 mM.

11. The kit of claim 1, wherein the non-ionic surfactant of the cleansing solution of (c) has a concentration of 0.025 to 0.1% (w/v).

12. The kit of claim 1, wherein a pH of the cleansing solution of (c) is 3 to 5.

13. A method for measuring a titer of a protein comprising human Fc using the kit of claim 1, the method comprising:
    (a) diluting a sample including the protein comprising a human Fc by using a mixture including 5 to 100 (w/v) % bovine serum, 0.05 to 0.2% (w/v) skim milk, and a non-ionic surfactant for dilution of sample;
    (b) reacting standard solutions diluted to various concentrations in the mixture including 5 to 100 (w/v) % bovine serum, 0.05 to 0.2% (w/v) skim milk, and a non-ionic surfactant for dilution of sample, in wells of a plate to which a target antigen is adsorbed;
    (c) suctioning contents of each of the wells and washing each of the wells with a cleansing solution including sodium acetate, sodium chloride, and a non-ionic surfactant;
    (d) completely removing the cleansing solution remaining in each of the wells, and adding a diluent for conjugate in each of the wells to be subjected to a reaction, said diluent for conjugate including an 10% (w/v) goat serum;
    (e) suctioning contents of each of the wells and washing each of the wells with the cleansing solution, said cleaning solution including sodium acetate, sodium chloride, and a non-ionic surfactant;
    (f) completely removing the cleansing solution remaining in each of the wells, and adding a substrate solution in each of the wells to be subjected to a reaction;
    (g) stopping the reaction by adding a solution for stopping reaction to each of the wells; and
    (h) measuring an absorbance of the standard solutions and the sample.

14. The method of claim 13, wherein the sample including the protein comprising a human Fc is one or more selected from the group consisting of human serum, human plasma and human blood.

15. The method of claim 13, wherein the non-ionic surfactant of the mixture of steps (a) and (b) has a concentration of 0.025 to 0.1% (w/v).

16. The method of claim 13, wherein the mixture of steps (a) and (b) further includes a preservative.

17. The method of claim 16, wherein the preservative is Proclin 300.

18. The method of claim 16, wherein the preservative has a concentration of 0.025 to 0.1% (w/v).

19. The method claim 13, wherein the goat serum of step (d) includes goat anti-human IgG.

20. The method of claim 19, wherein the goat anti-human IgG is specific to human Fc.

* * * * *